US012692477B2

(12) United States Patent
Lee et al.

(10) Patent No.: US 12,692,477 B2
(45) Date of Patent: Jul. 28, 2026

(54) MEDIUM COMPOSITION FOR CULTURING PORCINE PLURIPOTENT STEM CELLS

(71) Applicant: SPACE F CORP., Hwaseong-si (KR)

(72) Inventors: Chang Kyu Lee, Seoul (KR); Kwang Hwan Choi, Seoul (KR); Dong Kyung Lee, Seongnam-si (KR)

(73) Assignee: SPACE F CORP., Hwaseong-si (KR)

( * ) Notice: Subject to any disclaimer, the term of this patent is extended or adjusted under 35 U.S.C. 154(b) by 1009 days.

(21) Appl. No.: 17/124,823

(22) Filed: Dec. 17, 2020

(65) Prior Publication Data

US 2021/0102163 A1     Apr. 8, 2021

Related U.S. Application Data

(63) Continuation-in-part of application No. PCT/KR2019/007387, filed on Jun. 19, 2019.

(30) Foreign Application Priority Data

Jun. 19, 2018     (KR) ........................ 10-2018-0070478

(51) Int. Cl.
*C12N 5/0735*          (2010.01)

(52) U.S. Cl.
CPC ........ *C12N 5/0606* (2013.01); *C12N 2500/34* (2013.01); *C12N 2500/62* (2013.01); *C12N 2501/115* (2013.01); *C12N 2501/16* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 2012/0295351 A1* | 11/2012 | Sherley | C12N 5/0696 |
| | | | 435/377 |
| 2013/0273649 A1 | 10/2013 | Wu et al. | |
| 2017/0275593 A1* | 9/2017 | Hanna | C12N 5/0606 |
| 2020/0170241 A1* | 6/2020 | Wei | C07K 7/08 |

FOREIGN PATENT DOCUMENTS

| | | |
|---|---|---|
| EP | 2784152 A1 | 10/2014 |
| EP | 3266864 A1 | 1/2018 |
| KR | 10-2012-0117209 A | 10/2012 |
| KR | 10-2017-0036485 A | 4/2017 |
| WO | 2005/045007 A1 | 5/2005 |
| WO | 2011/140397 A2 | 11/2011 |

OTHER PUBLICATIONS

Wang et al (Scientific Reports | 6:27256 | DOI: 10.1038/srep27256, Published: Jun. 6, 2016) (Year: 2016).*
Son et al (Asian-Aust. J. Anim. Sci. vol. 22, No. 1 : Jan. 26-34, 2009, DOI: 10.5713/ajas.2009.80343) (Year: 2009).*
Korea Intellectual Property Office, Office Action for corresponding KR 10-2018-0070478, dated Mar. 21, 2019.
International Searching Authority, International Search Report for PCT/KR2019/007387, dated Oct. 18, 2019.
Tsukiyama et al., "A Modified EpiSC Culture Condition Containing a GSK3 Inhibitor Can Support Germline-Competent Pluripotency in Mice", Plos one, Apr. 2014, vol. 9, Issue 4, e95329, pp. 1-10, XP002803476 (10 pages total).

* cited by examiner

*Primary Examiner* — Peter Paras, Jr.
*Assistant Examiner* — Khoa Nhat Tran
(74) *Attorney, Agent, or Firm* — Sughrue Mion, PLLC

(57) ABSTRACT

A medium composition for porcine pluripotent stem cells, containing bFGF, activin A, CHIR99021 and IWR-1 is disclosed. The composition is prepared from specific ingredients, excluding non-specific ingredients, thereby facilitating quality control, and thus is suitable for the study of porcine pluripotent stem cells. Also disclosed is a method for culturing, maintaining and preserving porcine pluripotent stem cells having the ability to form teratomas, by using the composition.

17 Claims, 12 Drawing Sheets
(11 of 12 Drawing Sheet(s) Filed in Color)

Contraction Phase

Relaxation Phase

FIG. 7B

MEDIUM COMPOSITION FOR CULTURING PORCINE PLURIPOTENT STEM CELLS

CROSS REFERENCE TO RELATED APPLICATIONS

This application is a continuation-in-part of PCT/KR2019/007387 filed Jun. 19, 2019 claiming priority from Korean patent application no. KR 10-2018-0070478 filed Jun. 19, 2018.

TECHNICAL FIELD

The present disclosure relates to a medium for culturing, maintaining, and cryopreserving porcine pluripotent stem cells.

BACKGROUND ART

Stem cells refer to cells that have the capacity to self-reproduce and differentiate into various cells. Here, the differentiation capacity is divided into various levels depending on the stage. Among them, pluripotent stem cells capable of differentiating into all types of cells in the human body are undergoing a number of studies worldwide. To date, pluripotent stem cells have been established as embryonic stem cells, embryonic germ cells, and induced pluripotent stem cells. Since pluripotent stem cells can be differentiated into various cells and tissues, they are attracting attention as a tool for regenerative medicine and cell therapy. The differentiation capacity of these pluripotent stem cell lines could be verified through the formation of teratoma and chimera. In order to treat human diseases by differentiating pluripotent stem cells into various cells, preclinical studies using animals are essential. Preclinical studies start with rodents, which are small animals, then are conducted in large animals such as dogs, horses, pigs and others, and finally are performed in primates close to humans. However, to date, only pluripotent stem cells from rodents and primates have been established, and pluripotent stem cells from large animals have not been established, so preclinical studies have experienced difficulties.

The first established human and mouse embryonic stem cell lines were obtained from a culture medium based on fetal bovine serum. However, unidentified animal-derived components induce the differentiation of stem cells during culturing, presenting an obstacle to clinical application. Therefore, development of a chemically optimized culture medium of embryonic stem cell lines for stem cell research and clinical application was required.

In the case of pigs, in order to establish a preclinical model, attempts have been made to establish embryonic stem cell lines through various culture components since 1990. LIF, FGF2, IL, OSM, CNTF, EGF, ACT A, and SCF were used as signal molecules but failed to establish embryonic stem cells with teratoma- and chimera-forming capacity. Also, while the slightly differentiated form of embryonic stem-like cell lines succeeded in culturing in various laboratories, these cells did not have differentiation capacity in the body.

Among various large animals, pigs have been used as important animal models for preclinical studies because of the physiological and anatomical similarities to humans and their organs. Therefore, since the 1990s, many studies have been conducted to establish embryonic stem cell lines using porcine embryos. However, to date, porcine embryonic stem cell lines having in vivo differentiation capacity (teratoma and chimera formation ability) have not been established.

The present inventors completed the present disclosure by successfully culturing, maintaining, and cryopreserving porcine stem cells without the use of fetal bovine serum, which includes conventionally unidentified animal-derived components, and confirming that these stem cells have in vivo differentiation capacity.

DETAILED DESCRIPTION OF THE INVENTION

Technical Problem

It is a first purpose of the present disclosure to provide a composition for culturing porcine pluripotent stem cells.

A second purpose of the present disclosure is to provide a composition for maintaining porcine pluripotent stem cells.

A third purpose of the present disclosure is to provide a composition for cryopreserving porcine pluripotent stem cells.

A fourth purpose of the present disclosure is to provide a method for culturing, maintaining and cryopreserving porcine pluripotent stem cells.

Technical Solution

For the above-described purposes, a first aspect of the present disclosure provides a medium composition for porcine pluripotent stem cells, with the medium composition including, in a medium for culturing porcine stem cells, bFGF (basic fibroblast growth factor), activin A, CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), and IWR-1 (4-(1,3,3a,4,7,7a-Hexa-hydro-1,3-dioxo-4,7-methano-2H-isoindol-2-yl)-N-8-quinolinyl-Benzamide). Preferably, according to the medium composition for porcine pluripotent stem cells, the medium includes Dulbecco's Modified Eagle's Medium (DMEM), which includes a serum replacement as set forth in Tables 1-5, lipid concentrate (LC), L-alanine-L-glutamine, MEM nonessential amino acids (Gibco), antibacterial agents, antifungal agents, beta-mercaptoethanol, and in addition thereto, bFGF, activin A, CHIR99021 (6-[[2-[[4-(2,4-Dichlorophenyl)-5-(5-methyl-1H-imidazol-2-yl)-2-py-rimidinyl]amino]ethyl]amino]-3-pyridinecarbonitrile), and IWR-1 (4-(1,3,3a,4,7,7a-Hexahydro-1,3-dioxo-4,7-methano-2H-isoindol-2-yl)-N-8-quinolinyl-Benzamide). Commercially available products such as KNOCKOUT™ Serum Replacement (KSR; Gibco) can be used as a serum replacement.

More preferably, according to the medium composition for porcine pluripotent stem cells, in the medium, the allowable concentration of the bFGF is $3.03\times10^{-4}$ to $6.06\times10^{-3}$ μM, the concentration of the activin A is $1.50\times10^{-4}$ to $5.40\times10^{-4}$ μM, the concentration of the CHIR99021 is 0.5 to 2.50 μM, and the concentration of the IWR-1 is 1.20 to 3.00 μM. Even more preferably, according to the medium composition for culturing porcine pluripotent stem cells, the medium may be a KNOCKOUT™ Dulbecco's Modified Eagle's Medium (KO-DMEM; Gibco) culture solution composition which includes: about 20% (v/v) of bovine serum replacement as set forth in Tables 1-5; about 0.1% (v/v) of chemically defined lipid concentrate (LC; Gibco); about 1% (v/v) of L-alanine-L-glutamate; about 1% (v/v) of MEM nonessential amino acids (Gibco); about 1% (v/v) of antibiotics-antimycotics (Gibco); about 0.1 mM β-mercapto-ethanol (Gibco); about $6.06 \times 10^{-4}$ µM basic fibroblast growth factors (bFGFs); about $3.85 \times 10^{-4}$ µM activin A (Act A); about 0.5 µM CHIR99021; and about 1. µM IWR-1. The term "about" as used in the disclosure and the claims includes 10%, 9%, 8%, 7%, 6%, 5%, 4%, 3%, 2%, or 1% variation from the numerical value and, in a case written as a range, from the lower limit and from the upper limit of the ranges.

A second aspect of the present disclosure provides a medium composition for porcine pluripotent stem cells, with the medium composition including, in a medium for maintaining stem cells, bFGF, activin A, CHIR99021 (6-[[2-[[4-(2,4-Dichlorophenyl)-5-(5-methyl-1H-imidazol-2-yl)-2-py-rimidinyl]amino]ethyl]amino]-3-pyridinecarbonitrile); and IWR-1 (4-(1,3,3a,4,7,7a-Hexahydro-1,3-dioxo-4,7-methano-2H-isoindol-2-yl)-N-8-quinolinyl-Benzamide). Preferably, according to the medium composition for porcine pluripotent stem cells, the medium may include Dulbecco's Modified Eagle's Medium (DMEM) medium, which includes serum replacement, lipid concentrate, L-alanine-L-glutamine; MEM nonessential amino acids, antibacterial agents, antifungal agents and beta-mercaptoethanol, and in addition thereto, bFGF, activin A, CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), IWR-1 (4-(1,3,3a,4,7,7a-Hexahydro-1,3-dioxo-4,7-methano-2H-isoindol-2-yl)-N-8-quinolinyl-Benzamide). More preferably, according to the medium composition for porcine pluripotent stem cells, in the medium, the allowable concentration of the bFGF is $3.03 \times 10^{-4}$ to $6.06 \times 10^{-3}$ µM, the concentration of the activin A is $1.50 \times 10^{-4}$ to $5.40 \times 10^{-4}$ µM, the concentration of the CHIR99021 is 0.5 to 2.50 µM, and the concentration of the IWR-1 is 1.20 to 3.00 µM. Even more preferably, according to the medium composition for maintaining porcine pluripotent stem cells, the medium may be a culture medium solution composition which includes: about 15% (v/v) of a bovine serum replacement; about 0.1% (v/v) of chemically defined lipid concentrate; about 1% (v/v) of L-alanine-L-glutamine; about 1% (v/v) of MEM nonessential amino acids; about 1% (v/v) of antibiotics-antimy-cotics; about 0.1 mM β-mercaptoethanol; about $1.21 \times 10^{-3}$ µM basic fibroblast growth factor (bFGF); about $3.85 \times 10^{-4}$ µM activin A (Act A); about 1.5 µM CHIR99021 (6-[[2-[[4-(2,4-Dichlorophenyl)-5-(5-methyl-1H-imidazol-2-yl)-2-py-rimidinyl]amino]ethyl]amino]-3-pyridinecarbonitrile); and about 2.5 µM IWR-1 (4-(1,3,3a,4,7,7a-Hexahydro-1,3-di-oxo-4,7-methano-2H-isoindol-2-yl)-N-8-quinolinyl-Benz-amide).

A third aspect of the present disclosure is a composition for cryopreserving porcine pluripotent cells, with the composition including about 10% (v/v) of DMSO, about 10% (v/v) of ethylene glycol, and about 80% (v/v) of the composition for maintaining porcine pluripotent stem cells.

A fourth aspect of the present disclosure is a composition for cryopreserving porcine pluripotent stem cells, the composition including about 20% (v/v) of DMSO, about 20% (v/v) of ethylene glycol, about 0.5M sugar, and about 60% (v/v) of the composition for maintaining porcine pluripotent stem cells.

A fifth aspect of the present disclosure is a method for culturing porcine pluripotent stem cells using the composition for culturing porcine pluripotent stem cells.

A sixth aspect of the present disclosure is a method for maintaining porcine pluripotent stem cells using the composition for maintaining porcine pluripotent stem cells.

A seventh aspect of the present disclosure is a method for cryopreserving porcine pluripotent stem cells using the composition for cryopreserving porcine pluripotent stem cells.

Advantageous Effects

A culture medium prepared according to the present disclosure may be used for the establishment and culturing of porcine embryonic stem cells having in vivo differentiation capacity (teratoma-forming capacity). Porcine embryonic stem cells thus established may be utilized for construction of preclinical models in large animals, based on the in vivo differentiation capacity thereof, and may also be employed for production of transgenic animals through chimera formation. In addition, this technique may be utilized for the establishment of porcine induced pluripotent stem cells and embryonic germ cell lines, and it also may be applied to other species (dogs, cattle, horses, and others) for which embryonic stem cell lines have not yet been established.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is a view of a population obtained by long-term culturing of porcine inner cell mass in each culture solution. Scale bar=400 µm (FIG. 3C) Porcine embryonic stem cells showed activity of alkaline phosphatase. Scale bar=400 µm.

FIG. 4 shows the expression of pluripotent genes in porcine embryonic stem cells. Pluripotent genes, including OCT4, SOX2, NANOG, SSEA1, SSEA4, TRA-1-60 and TRA-1-81, were expressed in porcine embryonic stem cells as measured by immunostaining. Scale bar=200 µm.

FIG. 6A is a photograph showing the characteristic features of primitive neural cells, and FIG. 6B is a photograph stained with ZO1, one of the markers of neural rosette.

Figure 7A:
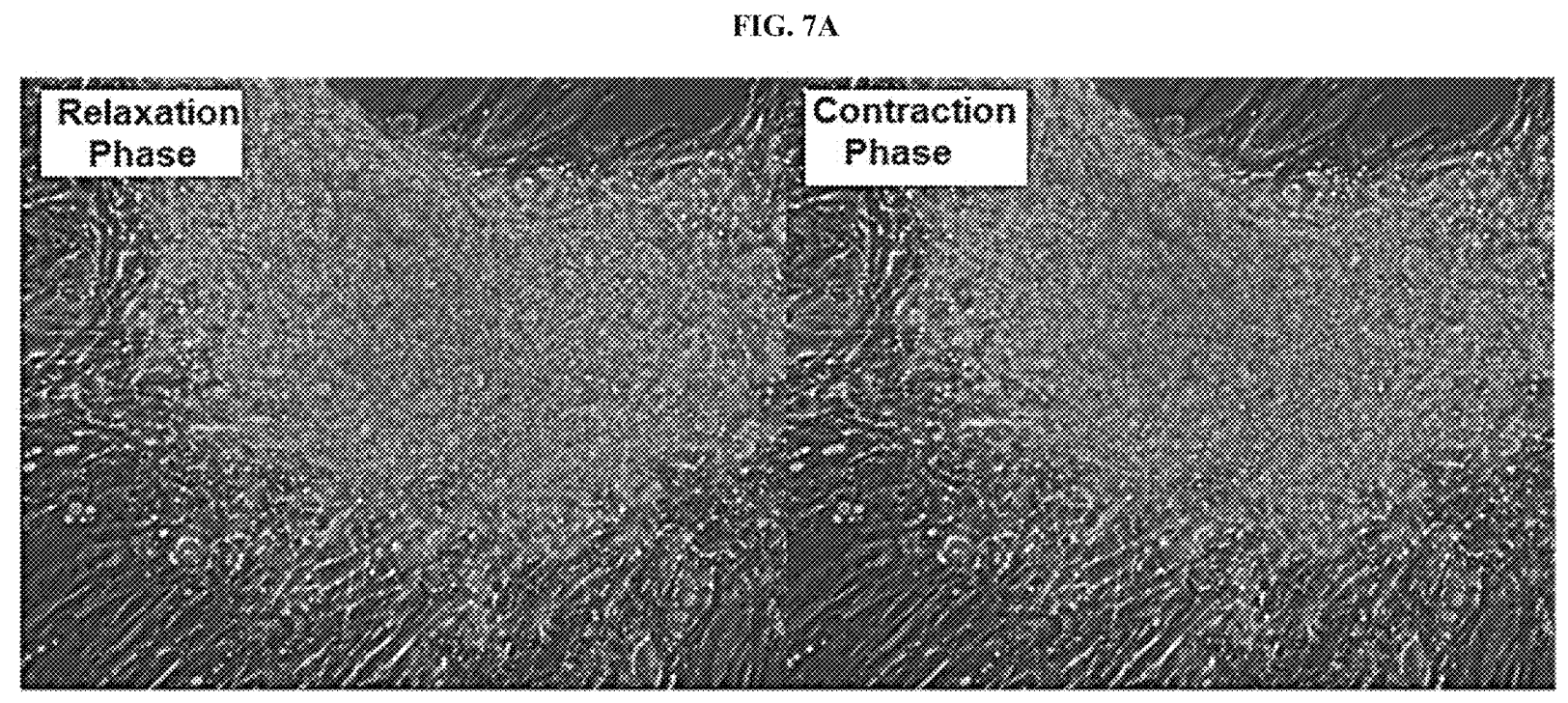
Figure 7B:
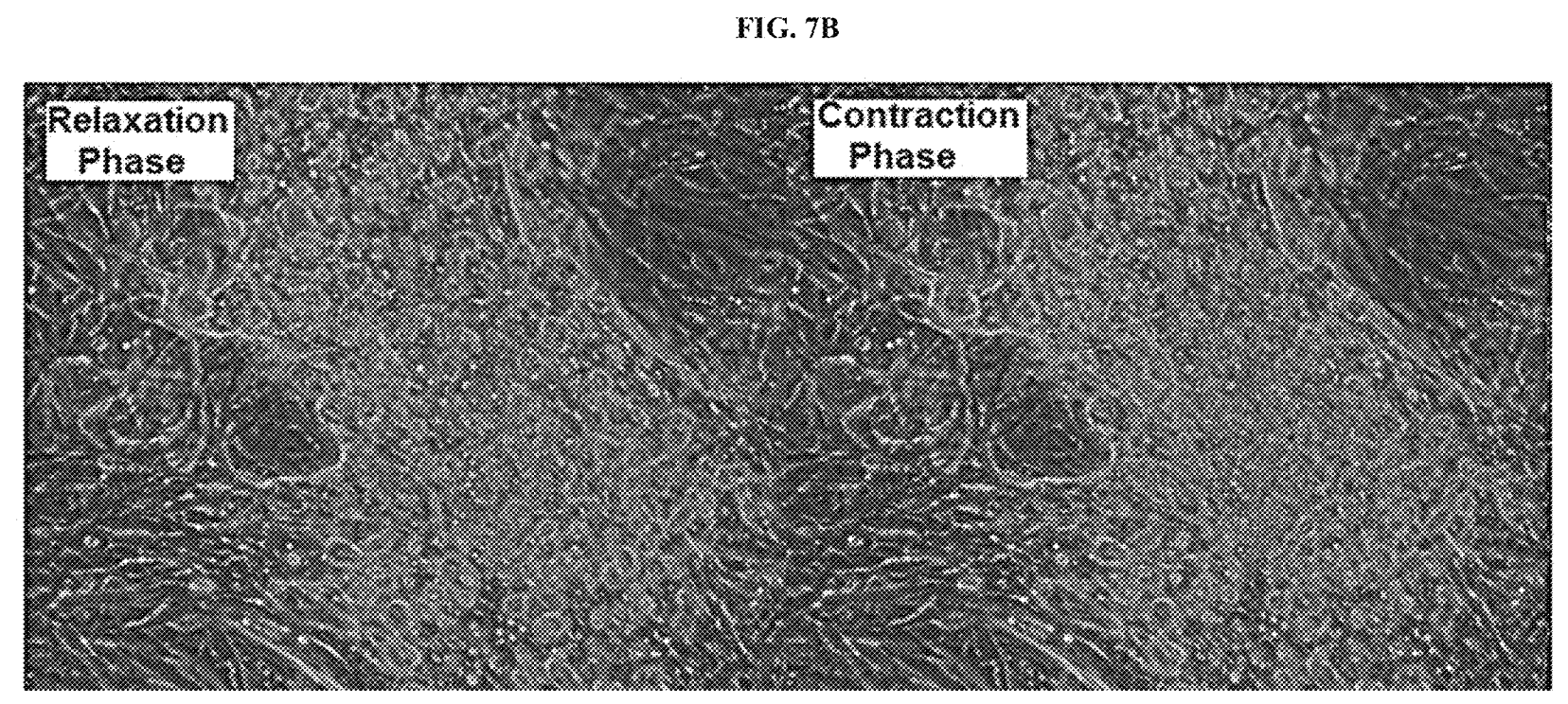

FIGS. 7A and 7B are photographs of directed differentiation of porcine embryonic stem cells into cardiomyocytes. The left photograph is a photograph showing the state of a relaxation phase, and the right photograph is a photograph showing the state of a contraction phase.

Figure 1:
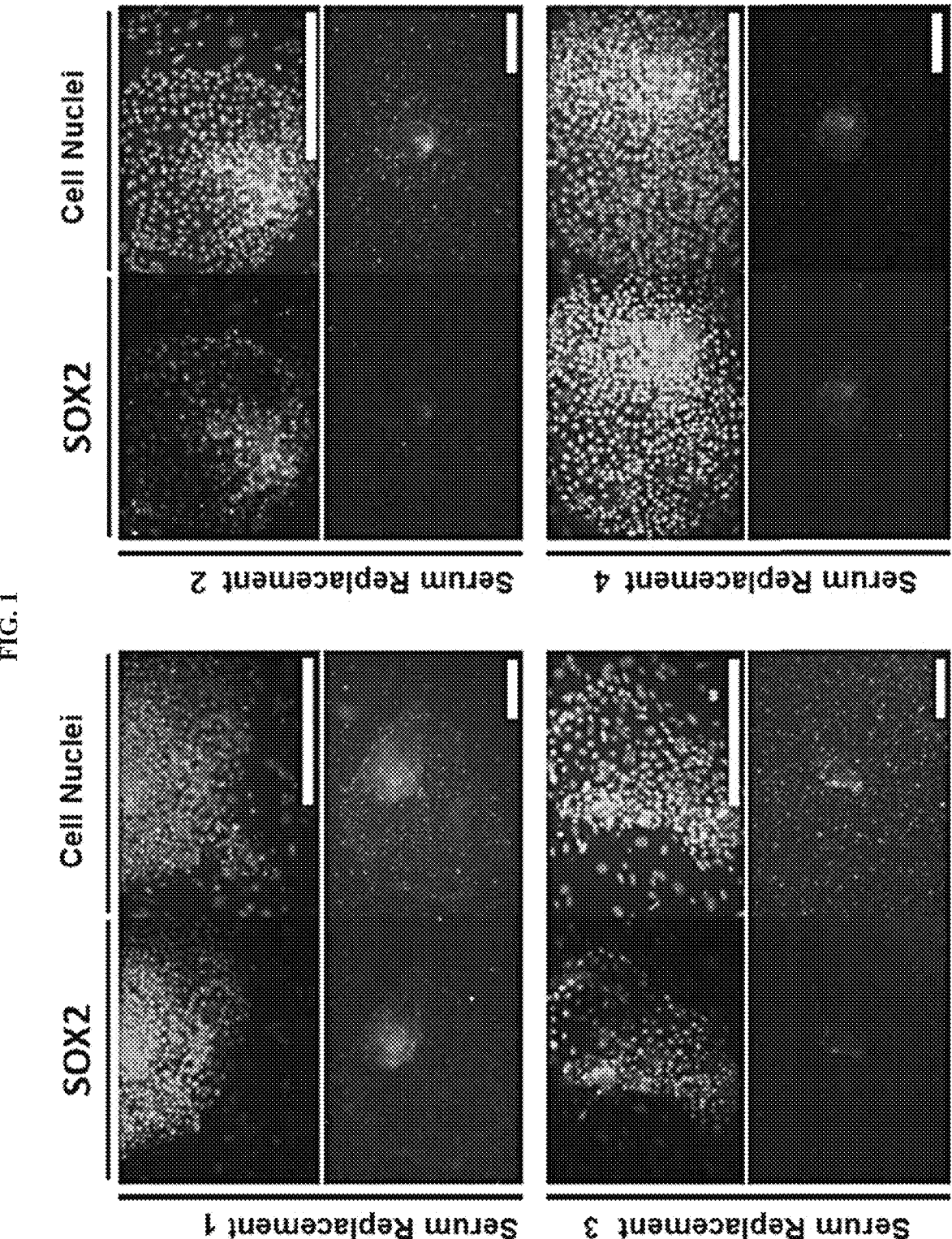
FIG. 1 is a datum confirming the expression of SOX2 by culturing porcine inner cell mass by using various serum replacements. Scale bar=200 µm

BEST MODE FOR CARRYING OUT THE INVENTION (Example 1) Composition of Culture Medium Used for Establishing and Maintaining Porcine Embryonic Stem Cells Embryonic stem cells are established through long-term culturing of the inner cell mass of blastocysts in vitro. Various serum replacements and signal molecules were used to develop a culture solution for maintaining porcine embryonic stem cells. Although fetal bovine serum has been used in various ways in cell culturing, since many unidentified substances are contained therein, serum replacements such as KSR, N2/B27, lipid complex (LC) and others were used to optimize the culture medium.

The composition of the serum replacement used is shown in Tables 1 to 5.

TABLE 1

Composition of Basal Culture Medium (Final Concentration in the Experiment)

| Component | Concentration (mM) |
|---|---|
| Inorganic Salt | |
| calcium chloride (anhydrous salt) | 1.38E+00 |
| magnesium sulfate (MgSO$_4$) | 6.24E−01 |
| potassium chloride (KCl) | 4.09E+00 |
| sodium bicarbonate (NaHCO$_3$) | 3.38E+01 |
| sodium chloride (NaCl) | 8.61E+01 |
| sodium phosphate, mono(NaH$_2$PO$_4$—H$_2$O) | 7.02E−01 |
| Trace Element | |
| ferric nitrate (Fe(NO$_3$)$_3$—9H$_2$O) | 1.90E−04 |
| Growth Factor | |
| bFGF | 6.06E−07 |
| Vitamin | |
| choline chloride | 2.19E−02 |
| D-calcium pantothenate | 6.43E−03 |
| folic acid | 6.96E−03 |
| i-inositol | 3.07E−02 |
| niacinamide | 2.52E−02 |
| pyridoxine hydrochloride | 1.49E−02 |
| riboflavin | 8.16E−04 |
| thiamine hydrochloride | 9.11E−03 |
| Energy Substrate | |
| D-glucose | 1.92E+01 |
| sodium pyruvate | 7.67E−01 |
| Amino Acid | |
| L-alanine | 1.00E−01 |
| L-alanine-L-glutamine | 2.00E+00 |
| L-arginine hydrochloride | 3.05E−01 |
| L-asparagine-H$_2$O | 1.00E−01 |
| L-aspartic acid | 1.00E−01 |
| L-cystine 2HCl | 1.54E−01 |
| L-glutamic acid | 1.00E−01 |
| glycine | 4.07E−01 |
| L-histidine-HCl—H$_2$O | 1.53E−01 |
| L-isoleucine | 6.15E−01 |
| L-leucine | 6.15E−01 |
| L-lysine hydrochloride | 6.12E−01 |
| L-methionine | 1.54E−01 |
| L-phenylalanine | 3.07E−01 |
| L-proline | 1.00E−01 |
| L-serine | 4.07E−01 |
| L-threonine | 6.12E−01 |
| L-tryptophan | 6.02E−01 |
| L-tyrosine 2Na 2H$_2$O | 3.05E−01 |
| L-valine | 6.16E−01 |
| Other Component | |
| phenol red | 3.06E−02 |
| 2-mercaptoethanol | 1.00E−01 |
| penicillin | 1.87E−01 |
| streptomycin | 1.72E−01 |
| amphotericin B | 2.71E−04 |

6

TABLE 2

Bovine Serum Replacement 1 (Final Concentration when Mixed in Basal Culture Medium)

| Component | Concentration (mM) |
|---|---|
| Trace element | |
| ammonium metavanadate (NH$_4$VO$_3$) | 5.60E−05 |
| manganous sulfate (MnSO$_4$ H$_2$O) | 1.01E−05 |
| ammonium molybdate | 1.00E−05 |
| NiSO$_4$ 6H2O | 4.95E−06 |
| sodium meta silicate (Na$_2$SiO$_3$ 9H$_2$O) | 4.93E−03 |
| SnC$_{l2}$ | 5.33E−06 |
| CdCl$_2$ | 6.22E−05 |
| CrCl3 | 9.41E−06 |
| Ag NO$_3$ | 5.00E−06 |
| AlCl$_3$ 6H$_2$O | 2.49E−05 |
| Ba (C$_2$H$_3$O$_2$)$_2$ | 4.99E−05 |
| CoCl$_2$ 6H$_2$O | 5.00E−05 |
| GeO$_2$ | 2.53E−05 |
| KBr | 5.04E−06 |
| Kl | 5.12E−06 |
| NaF | 5.00E−04 |
| RbCl | 5.00E−05 |
| ZrOCl$_2$ 8H$_2$O | 9.04E−05 |
| Vitamin | |
| ascorbic acid | 3.75E−01 |
| thiamine hydrochloride | 1.96E−02 |
| Protein | |
| human insulin | 3.44E−03 |
| human holo-transferrin | 1.40E−01 |
| bovine serum albumin | 2.00E+02 |
| Other Component | |
| glutathione (reduced form) | 5.93E−03 |
| selenium | 1.77E−04 |

TABLE 3

Bovine Serum Replacement 2 (Final Concentration when Mixed in Basal Culture Medium)

| Component | Concentration (mM) |
|---|---|
| Vitamin | |
| biotin | 5.12E−03 |
| DL alpha tocopherol acetate | 1.06E−03 |
| DL alpha-tocopherol | 1.16E−03 |
| vitamin A (acetic acid) | 1.52E−04 |
| Protein | |
| BSA, fatty acid free fraction V | 1.88E−02 |
| catalase | 5.00E−06 |
| recombinant human insulin | 1.13E−03 |
| human transferrin | 1.03E−02 |
| superoxide dismutase | 9.62E−06 |
| Fat | |
| linoleic acid | 1.78E−03 |
| linolenic acid | 1.80E−03 |
| Other Component | |
| corticosterone | 2.89E−05 |
| D-galactose | 4.16E−02 |
| ethanolamine HCl | 2.07E−04 |
| glutathione (reduced form) | 1.63E−03 |
| L-Carnitine HCl | 5.06E−03 |
| progesterone | 3.01E−05 |
| putrescine 2HCl | 1.5E−01 |
| sodium selenite | 6.62E−05 |
| T3 (triode-I-thyronine) | 1.49E−06 |

TABLE 4

Bovine Serum Replacement 3 (Final concentration when mixed in basal culture Medium)

| Component | Concentration (mM) |
|---|---|
| Trace Element | |
| ammonium metavanadate | 1.40E−05 |
| manganous sulfate | 2.51E−06 |
| ammonium molybdate | 2.51E−06 |
| NiSO$_4$ 6H$_2$O | 1.24E−06 |
| sodium meta silicate | 1.23E−03 |
| SnCl$_2$ | 1.33E−06 |
| CdCl$_2$ | 1.55E−05 |
| CrCl$_3$ | 2.35E−06 |
| Ag NO$_3$ | 1.25E−06 |
| AlC$_{l3}$ 6H$_2$O | 6.21E−06 |
| Ba (C$_2$H$_3$O$_2$)$_2$ | 1.25E−05 |
| CoCl$_2$ 6H$_2$O | 1.25E−05 |
| GeO$_2$ | 6.33E−06 |
| KBr | 1.26E−06 |
| Kl | 1.28E−06 |
| NaF | 1.25E−04 |
| RbCl | 1.25E−05 |
| ZrOCl$_2$ 8H$_2$O | 2.26E−05 |
| Protein | |
| human insulin | 1.99E−03 |
| human holo-transferrin | 4.53E−02 |
| bovine serum albumin | 5.00E+01 |
| catalase | 5.00E−06 |
| superoxide dismutase | 9.62E−06 |
| Vitamin | |
| ascorbic acid | 9.38E−02 |
| thiamine hydrochloride | 4.89E−03 |
| biotin | 5.12E−03 |
| DL alpha tocopherol acetate | 1.09E−03 |
| DL alpha-tocopherol | 1.16E−03 |
| vitamin A (acetic acid) | 1.52E−04 |
| Fat | |
| linoleic acid | 1.78E−03 |
| linolenic acid | 1.80E−03 |
| Other Component | |
| glutathione (reduced form) | 3.11E−03 |
| sodium selenium | 1.11E−04 |
| corticosterone | 2.89E−05 |
| D-galactose | 4.16E−02 |
| Ethanolamine HCl | 2.07E−04 |
| L-Carnitine HCl | 5.06E−03 |
| progesterone | 3.01E−05 |
| putrescine 2HCl | 1.50E−01 |
| T3 (triodo-1-thyronine) | 1.49E−06 |

TABLE 5

Bovine Serum Replacement 4 (Final Concentration when Mixed in Basal Culture Medium)

| Component | Concentration (mM) |
|---|---|
| Trace Element | |
| ammonium metavanadate | 5.60E−05 |
| manganous sulfate | 1.01E−05 |
| ammonium molybdate | 1.00E−05 |
| NiSO4 6H2O | 4.95E−06 |
| sodium meta silicate | 4.93E−03 |
| SnCl$_2$ | 5.33E−06 |
| CdCl$_2$ | 6.22E−05 |
| CrCl$_3$ | 9.41E−06 |
| Ag NO$_3$ | 5.00E−06 |
| AlCl$_3$ 6H$_2$O | 2.49E−05 |

TABLE 5-continued

Bovine Serum Replacement 4 (Final Concentration when Mixed in Basal Culture Medium)

| Component | Concentration (mM) |
|---|---|
| Ba (C$_2$H$_3$O$_2$)$_2$ | 4.99E−05 |
| CoCl$_2$ 6H$_2$O | 5.00E−05 |
| GeO$_2$ | 2.53E−05 |
| KBr | 5.04E−06 |
| Kl | 5.12E−06 |
| NaF | 5.00E−04 |
| RbCl | 5.00E−05 |
| ZrOCl$_2$ 8H$_2$O | 9.04E−05 |
| Vitamin | |
| ascorbic acid | 3.75E−01 |
| thiamine hydrochloride | 1.96E−02 |
| Protein | |
| human insulin | 3.44E−03 |
| human holo-transferrin | 1.40E−01 |
| bovine serum albumin | 2.00E+02 |
| Fat | |
| arachidonic acid | 6.57E−06 |
| cholesterol | 5.69E−04 |
| DL-alpha-tocopherol acetate | 1.48E−04 |
| linoleic acid | 3.57E−05 |
| linolenic acid | 3.59E−05 |
| myristic acid | 4.38E−05 |
| oleic acid | 3.54E−05 |
| palmitic acid | 3.90E−05 |
| palmitoleic acid | 3.93E−05 |
| stearic acid | 3.52E−05 |
| Other Component | |
| glutathione (reduced form) | 5.93E−03 |
| selenium | 1.77E−04 |
| pluronic F68 | 1.08E−02 |
| tween 80 | 1.68E−03 |

First, a culture medium including KSR, N2/B27, KSR+N2/B27, or KSR+LC was used to find a serum replacement suitable for the growth of porcine embryos. Each culture medium was treated during a stem cell derivation process by attaching porcine blastocysts to feeder cells, and after culturing for 7 days, the growth of inner cell mass was observed in vitro by staining with SOX2, a pluripotent marker. As a result, it was confirmed that the inner cell mass expressing SOX2 rapidly grew in the group treated with KSR and KSR+LC (FIG. 1). Second, for long-term culturing of the inner cell mass, signal molecules were treated in various combinations (Table 6 and Table 7).

TABLE 6

| | | | Blastocyst<br>initial | Sox2 positive<br>rate of the | Number of<br>embryonic stem cell |
|---|---|---|---|---|---|
| Experimental<br>group | Number of<br>replicates | Number of<br>blastocysts<br>used | growth<br>rate (%) | initial<br>population (%) | lines established in<br>the long-term culture |
| bFGF | 3 | 30 | 30.0 ± 5.8 | 30.0 ± 5.8 | 0 |
| bFGF + ActA | 3 | 30 | 40.0 ± 5.8 | 26.7 ± 6.7 | 0 |
| bFGF + CHIR | 3 | 30 | 46.7 ± 13.3 | 33.3 ± 12.0 | 0 |
| bFGF + CHIR + ActA | 3 | 30 | 43.3 ± 24.0 | 26.7 ± 14.5 | 0 |

Results of Blastocysts Cultured Using Serum Replacement 1

TABLE 7

| | | | Blastocyst<br>initial | Sox2 positive<br>rate of the | Number of<br>embryonic stem cell |
|---|---|---|---|---|---|
| Experimental<br>group | Number of<br>replicates | Number of<br>blastocysts<br>used | growth<br>rate (%) | initial<br>population (%) | lines established in<br>the long-term culture |
| bFGF | 3 | 29 | 51.5 ± 4.6 | 44.8 ± 2.9 | 0 |
| bFGF + ActA | 3 | 29 | 48.9 ± 10.6 | 45.6 ± 10.9 | 0 |
| bFGF + CHIR | 3 | 29 | 51.5 ± 4.6 | 48.1 ± 6.1 | 0 |
| bFGF + CHIR + ActA | 3 | 29 | 62.6 ± 11.5 | 52.6 ± 12.6 | 2 |

Results of Blastocysts Cultured Using Serum Replacement 4

Figure 2:
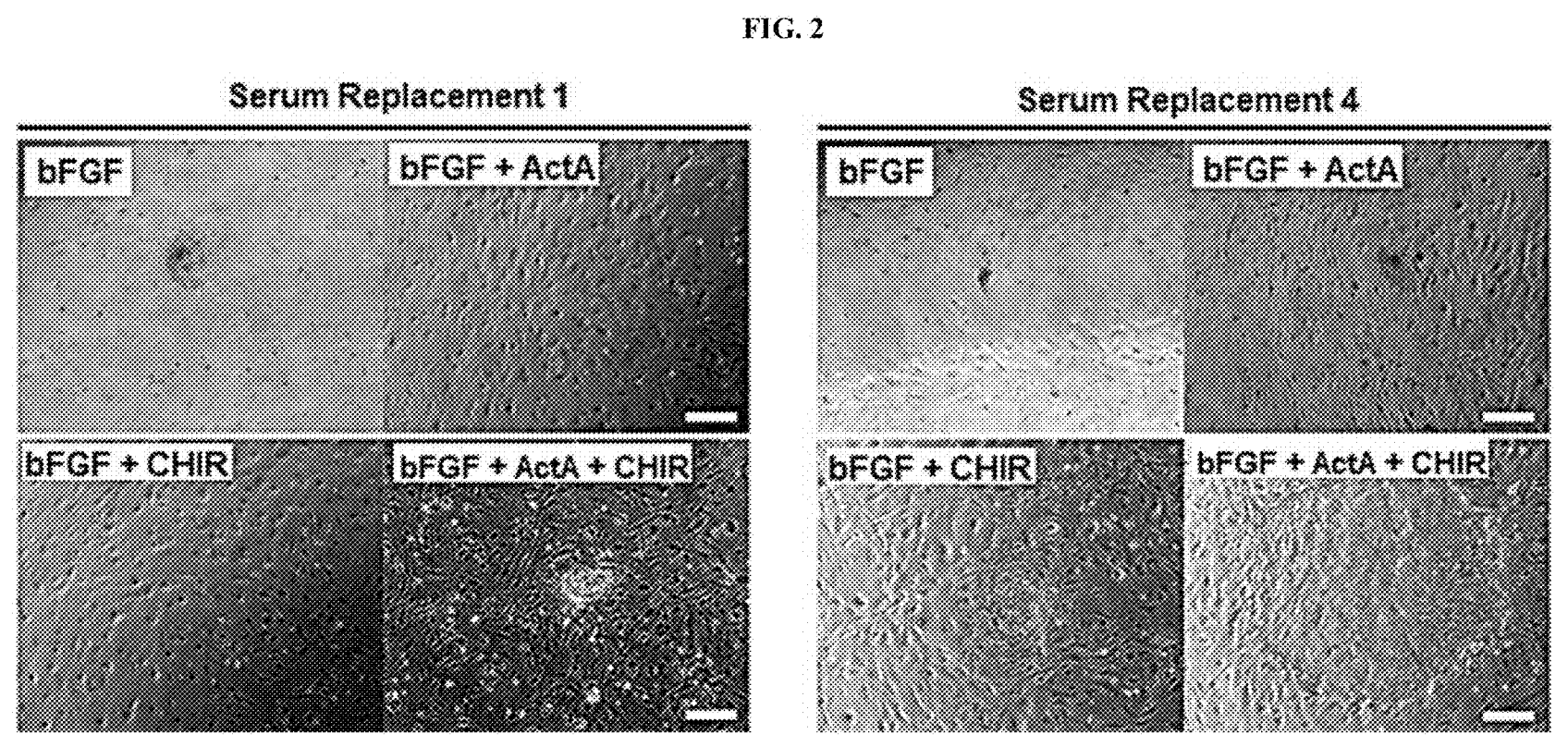

The culturing was attempted by adding signal molecules to basal medium including KSR or KSR+LC. Porcine embryonic stein cells were established in a culture medium including FGF2, A, and 6-[[2-[[4-(2,4-Dichlorophenyl)-5-(5-methyl-1H-imidazol-2-yl)-2-pyrimidinyl]amino]ethyl]amino]-3-pyridinecarbonitrile (CHIR99021) in a culture solution including serum replacement 4 (Tables 6 and 7, FIG. 2). In addition, for the stabilization of CHIR99021, 4-(1,3,3a,4,7,7a-Hexahydro-1,3-dioxo-4,7-methano-2H-isoindol-2-yl)-N-8-quinolinyl-Benzamide (IWR-1) was added to establish the composition for long-term culturing and maintenance of porcine embryonic stem cells, as shown in Table 8 and Table 9, respectively.

TABLE 8

Composition of Establishment Culture Medium
Acidity: pH 7.2-7.2; Osmotic Pressure: 330 mOsmo

| Component | Concentration<br>(mM) |
|---|---|
| Inorganic Salt | |
| calcium chloride (anhydrous salt) | 1.37E+00 |
| magnesium sulfate (MgSO$_4$) | 6.24E−01 |
| potassium chloride (KCl) | 4.09E+00 |
| sodium bicarbonate (NaHCO$_3$) | 3.38E+01 |
| sodium chloride (NaCl) | 8.61E+01 |
| sodium phosphate, mono(NaH$_2$PO$_4$—H$_2$O) | 7.02E−01 |
| Trace Element | |
| ferric nitrate | 1.90E−04 |
| ammonium metavanadate | 5.60E−05 |
| manganous Sulfate | 1.01E−05 |
| ammonium molybdate | 1.00E−05 |
| NiSO$_4$ 6H$_2$O | 4.95E−06 |
| sodium meta silicate | 4.92E−03 |
| SnCl$_2$ | 5.33E−06 |
| CdCl$_2$ | 6.22E−05 |
| CrCl$_3$ | 9.41E−06 |
| Ag NO$_3$ | 5.00E−06 |
| AlCl$_3$ 6H$_2$O | 2.49E−05 |
| Ba (C$_2$H$_3$O$_2$)$_2$ | 4.99E−05 |

TABLE 8-continued

Composition of Establishment Culture Medium
Acidity: pH 7.2-7.2; Osmotic Pressure: 330 mOsmo

| Component | Concentration<br>(mM) |
|---|---|
| CoCl$_2$ 6H$_2$O | 5.00E−05 |
| GeO$_2$ | 2.53E−05 |
| KBr | 5.04E−06 |
| KI | 5.12E−06 |
| NaF | 5.00E−04 |
| RbCl | 5.00E−05 |
| ZrOCl$_2$ 8H$_2$O | 9.04E−05 |
| Growth Factor | |
| bFGF | 6.06E−07 |
| activin A | 3.85E−07 |
| CHIR99021 | 5.00E−04 |
| endo-IWR-1 | 1.50E−03 |
| Fat | |
| linoleic acid | 3.57E−05 |
| arachidonic acid | 6.57E−06 |
| cholesterol | 5.69E−04 |
| DL-alpha tocopherol-acetate | 1.48E−04 |
| linolenic acid | 3.59E−05 |
| myristic acid | 4.38E−05 |
| oleic acid | 3.54E−05 |
| palmitic acid | 3.90E−05 |
| palmitoleic acid | 3.93E−05 |
| stearic acid | 3.52E−05 |
| Protein | |
| human insulin | 3.44E−03 |
| human holo-transferrin | 1.40E−01 |
| bovine serum albumin | 2.00E+02 |
| Amino Acid | |
| L-alanine | 1.00E−01 |
| L-alanine-L-glutamine | 2.00E+00 |
| L-arginine hydrochloride | 3.05E−01 |
| L-asparagine-H$_2$O | 1.00E−01 |
| L-aspartic acid | 1.00E−01 |
| L-cystine 2HCl | 1.54E−01 |
| L-glutamic acid | 1.00E−01 |

US 12,692,477 B2

11

TABLE 8-continued

Composition of Establishment Culture Medium
Acidity: pH 7.2-7.2; Osmotic Pressure: 330 mOsmo

| Component | Concentration (mM) |
|---|---|
| glycine | 4.07E−01 |
| L-histidine-HCl—H₂O | 1.53E−01 |
| L-isoleucine | 6.15E−01 |
| L-leucine | 6.15E−01 |
| L-lysine hydrochloride | 6.12E−01 |
| L-methionine | 1.54E−01 |
| L-phenylalanine | 3.07E−01 |
| L-proline | 1.00E−01 |
| L-serine | 4.07E−01 |
| L-threonine | 6.12E−01 |
| L-tryptophan | 6.02E−02 |
| L-tyrosine 2Na 2H₂O | 3.05E−01 |
| L-valine | 6.16E−01 |
| Vitamin | |
| ascorbic acid | 3.75E−01 |
| choline chloride | 2.19E−02 |
| D-calcium pantothenate | 6.43E−03 |
| folic acid | 6.96E−03 |
| i-inositol | 3.07E−02 |
| niacinamide | 2.52E−02 |
| pyridoxine hydrochloride | 1.49E−02 |
| riboflavin | 8.16E−04 |
| thiamine hydrochloride | 2.87E−02 |
| Energy Substrate | |
| D-glucose | 1.92E+01 |
| sodium pyruvate | 7.67E−01 |
| Other Component | |
| glutathione(reduced form) | 5.93E−03 |
| phenol red | 3.06E−02 |
| 2-mercaptoethanol | 1.00E−01 |
| selenium | 1.77E−04 |
| penicillin | 1.87E−01 |
| streptomycin | 1.72E−01 |
| amphotericin B | 2.71E−04 |
| pluronic F-68 | 1.08E−02 |
| tween 80 | 1.68E−03 |

TABLE 9

Composition of the Maintenance Culture Medium
Acidity: pH 7.2-7.2; Osmotic Pressure: 320 mOsmo

| Component | Concentration (mM) |
|---|---|
| Inorganic Salt | |
| calcium chloride (anhydrous salt) | 1.46E+00 |
| magnesium sulfate (MgSO₄) | 6.64E−01 |
| potassium chloride (KCl) | 4.36E+00 |
| sodium bicarbonate (NaHCO₃) | 3.60E+01 |
| sodium chloride (NaCl) | 9.16E+01 |
| sodium phosphate, mono (NaH₂PO₄—H₂O) | 7.48E−01 |
| Trace Element | |
| ferric nitrate | 2.00E−04 |
| ammonium metavanadate | 4.20E−05 |
| manganous sulfate | 7.50E−06 |
| ammonium molybdate | 7.50E−06 |
| NiSO₄ 6H₂O | 3.70E−06 |
| sodium meta silicate | 3.69E−03 |
| SnCl₂ | 4.00E−06 |
| CdCl₂ | 4.70E−05 |
| CrCl₃ | 7.10E−06 |
| Ag NO₃ | 3.80E−06 |
| AlCl₃ 6H₂O | 1.90E−05 |
| Ba (C₂H₃O₂)₂ | 3.70E−05 |
| CoCl₂ 6H₂O | 3.80E−05 |

12

TABLE 9-continued

Composition of the Maintenance Culture Medium
Acidity: pH 7.2-7.2; Osmotic Pressure: 320 mOsmo

| Component | Concentration (mM) |
|---|---|
| GeO₂ | 1.90E−05 |
| KBr | 3.80E−06 |
| KI | 3.80E−06 |
| NaF | 3.80E−04 |
| RbCl | 3.80E−05 |
| ZrOCl₂ 8H₂O | 6.80E−05 |
| Growth Factor | |
| bFGF | 1.21E−06 |
| activin A | 3.85E−07 |
| CHIR99021 | 1.50E−03 |
| endo-IWR-1 | 2.50E−03 |
| Fat | |
| linoleic acid | 3.60E−05 |
| arachidonic acid | 6.60E−06 |
| cholesterol | 5.70E−04 |
| DL-alpha tocopherol-acetate | 1.50E−04 |
| linolenic acid | 3.60E−05 |
| myristic acid | 4.40E−05 |
| oleic acid | 3.50E−05 |
| palmitic acid | 3.90E−05 |
| palmitoleic acid | 3.90E−05 |
| stearic acid | 3.50E−05 |
| Protein | |
| human insulin | 2.58E−03 |
| human holo-transferrin | 1.05E−01 |
| bovine serum albumin | 1.50E+02 |
| Amino Acid | |
| L-alanine | 1.00E−01 |
| L-alanine-L-glutamine | 2.00E+00 |
| L-arginine hydrochloride | 3.25E−01 |
| L-asparagine-H₂O | 1.00E−01 |
| L-aspartic acid | 1.00E−01 |
| L-cystine 2HCl | 1.64E−01 |
| L-glutamic acid | 1.00E−01 |
| glycine | 4.27E−01 |
| L-histidine-HCl—H₂O | 1.63E−01 |
| L-isoleucine | 6.55E−01 |
| L-leucine | 6.55E−01 |
| L-lysine hydrochloride | 6.52E−01 |
| L-methionine | 1.65E−01 |
| L-phenylalanine | 3.27E−01 |
| L-proline | 1.00E−01 |
| L-serine | 4.27E−01 |
| L-threonine | 6.52E−01 |
| L-tryptophan | 6.41E−02 |
| L-tyrosine 2Na 2H₂O | 3.25E−01 |
| L-valine | 6.57E−01 |
| Vitamin | |
| ascorbic acid | 2.81E−01 |
| choline chloride | 2.34E−02 |
| D-calcium pantothenate | 6.85E−03 |
| folic acid | 7.41E−03 |
| i-inositol | 3.27E−02 |
| niacinamide | 2.68E−02 |
| pyridoxine hydrochloride | 1.59E−02 |
| riboflavin | 8.70E−04 |
| thiamine hydrochloride | 2.44E−02 |
| Energy Substrate | |
| D-glucose | 2.04E+01 |
| sodium pyruvate | 8.17E−01 |
| Other Component | |
| glutathione(reduced form) | 4.45E−03 |
| phenol red | 3.26E−02 |
| 2-mercaptoethanol | 1.00E−01 |
| selenium | 1.30E−04 |
| penicillin | 1.87E−01 |
| streptomycin | 1.72E−01 |

TABLE 9-continued

| Composition of the Maintenance Culture Medium Acidity: pH 7.2-7.2; Osmotic Pressure: 320 mOsmo | |
| --- | --- |
| Component | Concentration (mM) |
| amphotericin B | 2.70E−04 |
| pluronic F-68 | 1.08E−02 |
| tween 80 | 1.68E−03 |

An early embryonic development process in which inner cell mass with pluripotency is formed has specificity for each species. In particular, pigs, unlike humans and mice, take a very long time in this process, and different cell signal transduction systems and metabolites are involved in the formation and maintenance of inner cell mass. Therefore, in order to establish embryonic stem cell lines by culturing the inner cell mass in vitro, it is essential to develop a culture medium including porcine specific signal molecules and metabolites. In this study, sequential experiments were conducted to develop a medium including FGF2, Act A, CHIR99021 and IWR-1 in a basal medium including that may maintain porcine embryonic stem cell lines.

Although previous studies have shown that Act A plays an important role in the maintenance of human embryonic stem cells and that CHIR99021 may be used to maintain pluripotency when used in culturing embryonic stem cells from humans and mice, it was not an essential element in culturing embryonic stem cells from mice and humans. However, the present inventors confirmed that in pig's, signal molecules such as Act A, CHIR99021, and IWR-1, along with FGF2, are essential for culturing embryonic stem cells. It was also confirmed that a lipid metabolism is essential for the growth of inner cell mass and maintenance of embryonic stem cells. Consequently, it was confirmed that additional signal molecules and metabolites are essential for the culture of porcine embryonic stem cell lines.

1. Composition of Establishment Culture Medium

A KNOCKOUT™ Dulbecco's Modified Eagle's Medium (KO-DMEM; Gibco) including 20% (v/v) of KNOCK-OUT™ Serum Replacement (KSR; Gibco), 0.1% (v/v) of chemically defined lipid concentrate (LC; Gibco), 1% (v/v) of GLUTAMAX™ (Gibco), 1% (v/v) of MEM nonessential amino acids (Gibco), 1% (v/v) of antibiotics-antimycotics (Gibco), 0.1 mM β-mercaptoethanol (Gibco), 10 ng/ml basic fibroblast growth factors (bFGFs), 5 ng/ml activin A (Act A), 0.5 μM CHIR99021, and 1.5 μM IWR-1 was used as a basal culture solution to derive porcine embryonic stem cells.

2. Composition of Maintenance Culture Medium

A KO-DMEM including 15% (v/v) of KSR (Gibco), 0.1% (v/v) of LC (Gibco), 1% (v/v) of Glutamax™, 1% (v/v) of MEM nonessential amino acids, 1% antibiotic-antimycotic, 0.1 mM β-mercaptoethanol, 20 ng/ml bFGF, 5 ng/ml Act, 1.5 μM CHIR99021, and 2.5 μM IWR-1 was used as a basal culture solution to culture porcine embryonic stem cells.

3. Composition of Freezing Culture Medium

Freezing solution 1: 10% (v/v) of DMSO, 10% (v/v) of ethylene glycol, 80% (v/v) of the maintenance culture medium Freezing solution 2: 20% (v/v) of DMSO, 20% (v/v) of ethylene glycol, 0.5M sugar, 60% (v/v) of the maintenance culture medium.

(Example 2) Effect of Growth Factor Concentration in Porcine Pluripotent Stem Cell Culture Medium The influence of a growth factor concentration in a porcine pluripotent stem cell culture medium established in the above-described example was analyzed, and the results are shown in Table 10.

TABLE 10

| Influence of Additional Growth Factor Concentration | | | | | | |
| --- | --- | --- | --- | --- | --- | --- |
| Growth factor | Used concentration (mM) | Optimal concentration (mM) | Role | Alternative substance | Symptoms when below the appropriate concentration | Symptoms when exceeding the appropriate concentration |
| bFGF | 3.03E−07~ 6.06E−06 | 1.21E−06 | Involved in promoting the growth of stem cells and maintaining pluripotency through the ERK signal transduction system. | | establishment efficiency of cell line is very low and cell differentiation occurs. | No specific symptom |
| activin A | 1.50E−07~ 5.40E−07 | 3.85E−07 | Involved in promoting the growth of stem cells and maintaining pluripotency through the SMAD signal transduction system. | | | Cell death |
| CHIR99021 | 5.00E−04~ 250E−03 | 1.50E−03 | Maintaining pluripotency by activating beta-catenin through inhibition of GSK3. | Alternativeness as GSK3 inhibitor such as BIO, lithium chloride (LiCl), and kenpaullone | | |
| IWR-1 | 1.20E−03~ 3.00E−03 | 2.50E−03 | Stabilizing beta-catenin | XAV or the like | | |

TABLE 10-continued

| | | | | | | |
|---|---|---|---|---|---|---|
| | | | Influence of Additional Growth Factor Concentration | | | |
| Growth factor | Used concentration (mM) | Optimal concentration (mM) | Role | Alternative substance | Symptoms when below the appropriate concentration | Symptoms when exceeding the appropriate concentration |
| | | | through Axin protein activation | | | |

When the concentration of growth factors was low, the growth of stem cells was reduced, and when the concentration of growth factor was high, except for bFGF, cells were killed. The allowable concentration of the bFGF was $3.03 \times 10^{-4}$ to $6.06 \times 10^{-3}$ μM, and the optimal concentration was $1.21 \times 10^{-3}$ μM. The allowable concentration of the Activin A was $1.50 \times 10^{-4}$ to $5.40 \times 10^{-4}$ μM, and the optimal concentration was $3.85 \times 10^{-4}$ μM. The allowable concentration of the CHIR99021 was 0.5 to 2.50 μM, and the optimal concentration was 1.50 μM. The allowable concentration of the IWR-1 was 1.20 to 3.00 μM, and the optimal concentration was 2.50 μM.

(Example 3) Derivation of Embryonic Stem Cell Line from Porcine Blastocysts

1. Immature Oocyte Recovery and In Vitro Maturation

The ovaries of sows slaughtered at the slaughterhouse were recovered, placed in a physiological saline solution at 25-30° C., and transported to the laboratory, and then the follicle fluid was aspirated and collected from a follicle 3-6 mm in diameter by a syringe attached with an 18 gauge needle. The collected oocytes were washed twice with TL-HEPES-PVA solution added with a 0.1% (w/v) of polyvinyl alcohol (PVA) and then used for oocyte maturation only after selecting ones of which the cumulus cells were uniform and the cytoplasm was homogeneous under a stereoscopic microscope. For maturation culturing of follicular eggs, culturing was carried out in TCM-199 added with 0.6 mM of cysteine, 10 ng/mL of epidermal growth factors (EGFs), 1 mg/ml of insulin, 4 IU/ml of Q6 equine chorionic gonadotropin (eCG), human chorionic gonadotropin (hCG), and 10% (v/v) of porcine follicular fluids (PFFs) for 22 hours, transferred to a culture solution to which the hormone was not added, and then cultured for 20 hours.

2. Production of Parthenogenetic Embryos Using In Vitro Mature Oocyte

After in vitro maturation culturing, the follicular eggs were placed in 0.1% hyaluronidase and vortexed for 3 minutes to remove the cumulus cells. A mature oocytes were washed in a phosphate buffered saline-bovine serum albumin (PBS-BSA) medium and subjected to electronic activation in a medium including mannitol at an intensity of 2.2 kV/cm for 30 μs to induce division of the oocytes. Then, culturing was carried out in a porcine zygote medium (PZM-3) containing 6-dimethylaminopurine (6-DMAP) for 4 hours, followed by 7 days in PZM-3 without 6-DMAP to obtain blastocysts. In order to hatch blastocysts, serum was added to the PZM-3 4 days after induction of division.

3. Production of Fertilized Eggs In Vitro

After in vitro maturation culturing, the follicular eggs were placed in 0.1% hyaluronidase and vortexed for 3 minutes to remove the cumulus cells. A mature oocytes were washed in a phosphate buffered saline-bovine serum albumin (PBS-BSA) medium and then used for in vitro fertilization. Semen for in vitro fertilization was centrifuged (500×g), the supernatant was removed, washed 3 times with a PBS solution added with 0.04% BSA, and then diluted with modified Tris-buffered medium (mTBM) solution. In vitro fertilization (4 hours) was induced by injecting the sperm to be $5 \times 10^5$ sperm/ml in the medium for in vitro fertilization. Then, it was transferred to a PZM-3 and cultured for 7 days under conditions of 5% $CO_2$, 5% $O_2$ and 39° C. to obtain blastocysts. In order to hatch blastocysts, serum was added to the PZM-3 4 days after induction of division.

4. Production of Feeder Cells Using Mouse Embryonic Fibroblasts

Mouse embryonic fibroblasts were isolated from the 14-day-old fetusespostcoitum. The extracted fetus had its head, limbs, and internal organs removed and then cut into small pieces. Fragmented fetal tissue was cultured in Dulbecco's Modified Eagle's Medium (DMEM; Welgene) including 10% (v/v) of bovine serum, 1% (v/v) of GLUTA-MAX™, 1% (v/v) of antibiotic-antimycotic, and 0.1 mM of β-mercaptoethanol. The sufficiently grown mouse embryonic fibroblasts were prepared at a concentration of 4-6× $10^5/cm^2$ (area of the culture dish) by treatment with an anti-mitotic agent such as mitomycin C.

5. Establishment of Porcine Embryonic Stem Cell Line Using In-Vitro-Produced Blastocysts (Parthenogenetic Embryos, In Vitro Fertilized Embryos)

Figure 3A:
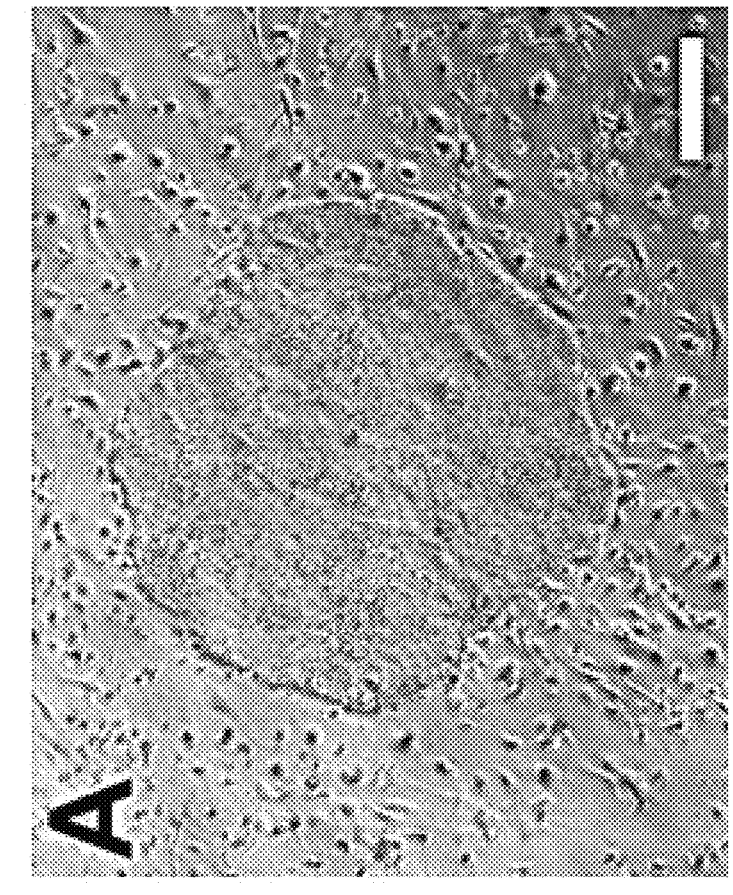
FIGS. 3A-3C show the morphology of porcine embryonic stem cells derived from a chemically defined medium. New embryonic stem cells were formed in a KSR+LC medium supplemented with FGF2+ActA+CH+IWR (FIG. 3A, FIG. 3B). Colonies of newly induced embryonic stem cells showed flat morphology, one cell of which showed epithelial morphology with a high nucleus-to-cytoplasmic ratio.
Figure 3B:
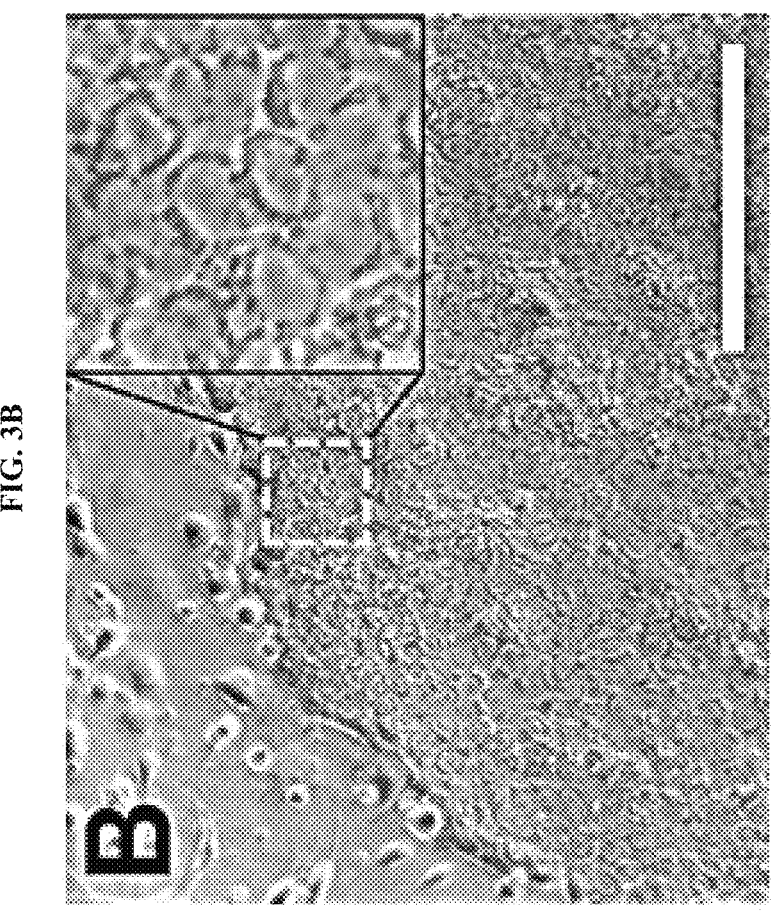
Figure 3C:
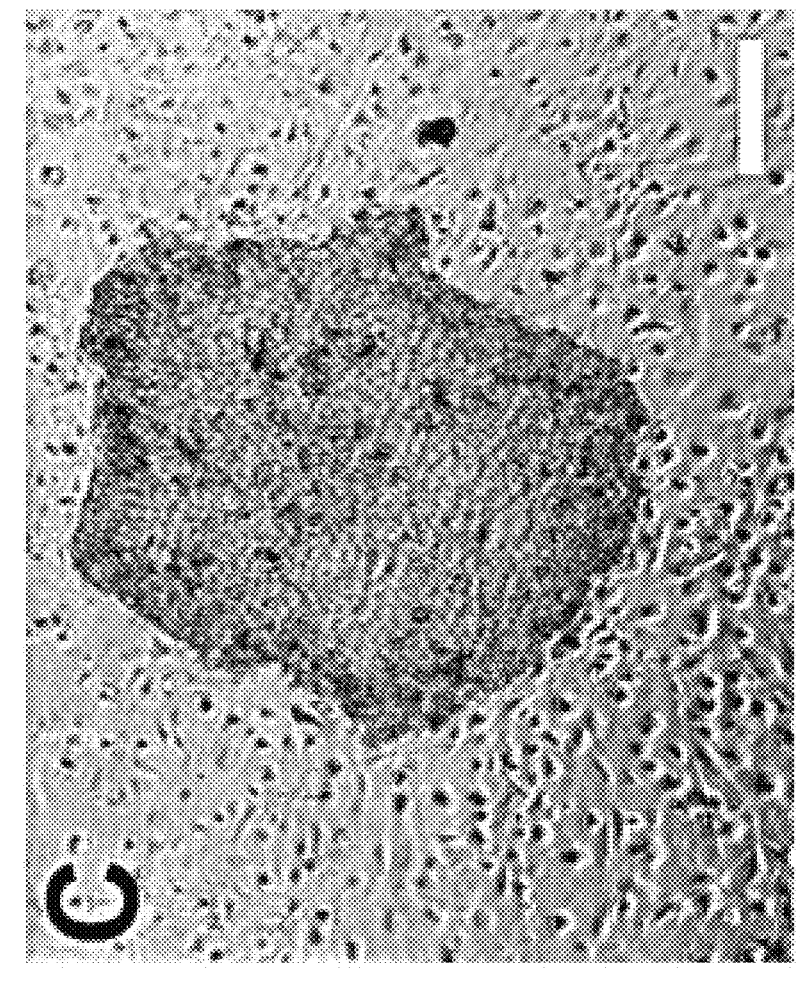

The previously produced hatched blastocysts were cultured for 2 days under conditions of 5% $CO_2$, 5% $O_2$, and 38° C. with feeder cells using a maintenance culture medium. During the initial two days of culturing, the culture solution was not replaced. On the third day of culturing, the culture solution was replaced with fresh maintenance culture solution, transferred to the condition of 5% $CO_2$, 37° C. and cultured for additional 5-6 days. The cluster of early embryonic stem cells that have been sufficiently grown was conducted to passage and conducted to further experiments. The established porcine embryonic stem cell line was grown in colony as a single cell layer, and the shape of the cells showed the characteristic of an embryonic stem cell line with a high ratio of nucleus and cytoplasm due to rapid division (FIGS. 3A-3C).

Figure 4:
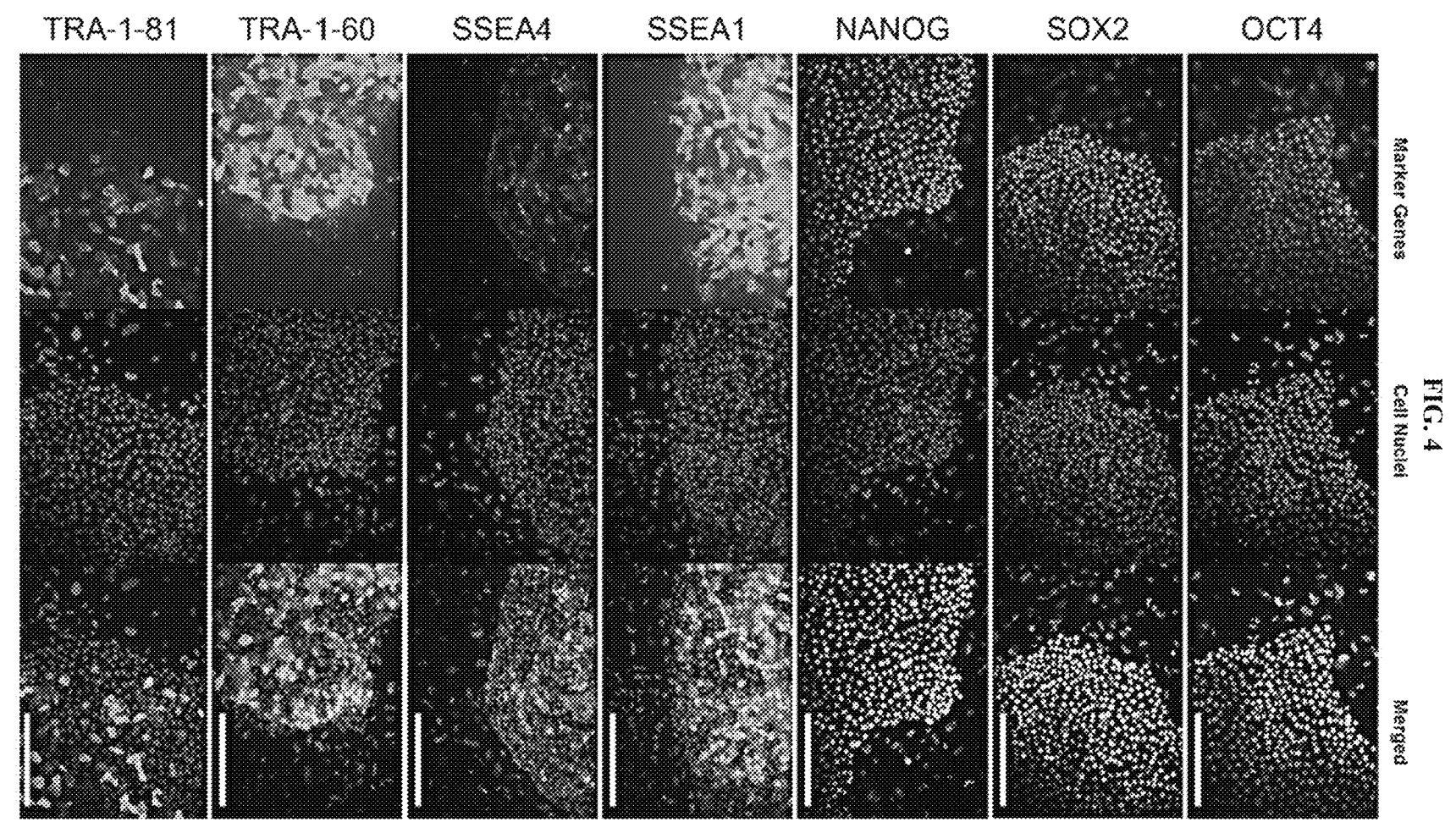

The established porcine embryonic stem cell line had the shape of a flat single cell layer similar to that of human embryonic stem cell lines, and expressed the pluripotent genes of OCT4, SOX2, NANOG, SSEA1, SSEA4, TRA-1-60, TRA-1-81, and AP. The newly established porcine embryonic stem cell line had a cluster shape of single cell layers similar to human embryonic stem cell lines, and had pluripotent genes such as OCT4, SOX2, NANOG and others (FIG. 4). In addition, it was confirmed that these cells were derived from the inner cell mass through the strong expression of SOX2 and SSEA1, which were specifically expressed in the inner cell mass present in the porcine blastocyst.

(Example 4) Maintaining the Established Porcine Embryonic Stem Cell Line

1. Passage and Maintenance of Porcine Embryonic Stem Cells

The sufficiently grown colony of porcine embryonic stem cells was conducted to passage and transferred to fresh feeder cells to culture. Porcine embryonic stem cells were treated with 10 μM of Y-27632 for 24 hours and then washed with Dulbecco's phosphate-buffered saline (DPBS; Welgene). The washed embryonic stem cell line was treated with a 0.25% trypsin/EDTA solution for 4 minutes and cut into small pieces by manipulation with a pipette. Only the cells were isolated through centrifugation (2,000 rpm, 3 minutes), and then culturing was carried out under conditions of 5% $CO_2$ and 37° C. together with fresh feeder cells using a maintenance culture solution including 10 μM of Y-27632. After 24 hours, the maintenance culture solution without Y-27632 was exchanged daily for 4-6 days and additional culturing is carried out.

(Example 5) Cryopreservation of Porcine Embryonic Stem Cells

Freezing: Porcine embryonic stem cells were treated with 10 μM of Y-27632 for 48 hours and then washed with Dulbecco's phosphate-buffered saline (DPBS; Welgene). The washed embryonic stem cell line was treated with a 0.25% trypsin/EDTA solution for 4 minutes and cut into small clumps by manipulation with a pipette. The supernatant was removed by centrifugation (2,000 rpm, 3 minutes) to isolate only the cells, and the cells were re-suspended in 50 μl of freezing solution 1. Freezing solution 1 was added, and after 1 minute, 250 μl of freezing solution 2 was added while being slowly mixed. Freezing solution 2 was added and incubated for 1 minute, and then the cells were transferred to liquid nitrogen to be frozen.

Thawing: The frozen porcine embryonic stem cells were taken out from the liquid nitrogen, and 700 μl of freezing solution 2 at 37° C. was dissolved while being rapidly mixing. To the same, 5 ml of a maintenance culture solution at 37° C. was added while being slowly mixed. Only the cells were isolated through centrifugation (2,000 rpm, 3 minutes), and then culturing was carried out under conditions of 5% $CO_2$ and 37° C. together with fresh feeder cells using a maintenance culture solution containing 10 μM of Y-27632. After 24 hours, the maintenance culture solution without Y-27632 was exchanged daily for 4-6 days and additional culturing is carried out.

This method may also be replaced by commercially available MFRESR™ (Stem cell technology, 05855).

(Example 6) Verification of Expression of Pluripotency Genes in Porcine Embryonic Stem Cells The porcine embryonic stem cell lines were fixed with 4% paraformaldehyde for 30 minutes, and then washed twice with DPBS. In order to observe the activity of alkaline phosphatase in fixed cells, a BCIP/NBT solution was treated for 30 minutes, washed twice with DPBS, and observed through a microscope. For immunological staining, the fixed cells were treated with 0.1% triton x-100 for 15 minutes and treated using 10% goat serum for 1 hour at room temperature. Then, primary antibodies that recognize pluripotency genes (anti-OCT4, SOX2, NANOG, SSEA1, SSEA4, TRA-1-60, and TRA-1-81) were reacted with the fixed porcine embryonic stem cells at a concentration of 1:200 for 15 hours at 4° C. After the primary antibody treatment, the secondary antibody coupled to the fluorescent substance was treated at room temperature for 2 hours, and then fluorescence was observed with a fluorescence microscope. As a result of observation, expression of alkaline phosphatase was confirmed in the porcine embryonic stem cell lines (FIG. 3), and expressions of OCT4, SOX2, NANOG, SSEA1, SSEA4, TRA-1-60, and TRA-1-81, which are pluripotency genes was confirmed (FIG. 4).

Figure 5A:
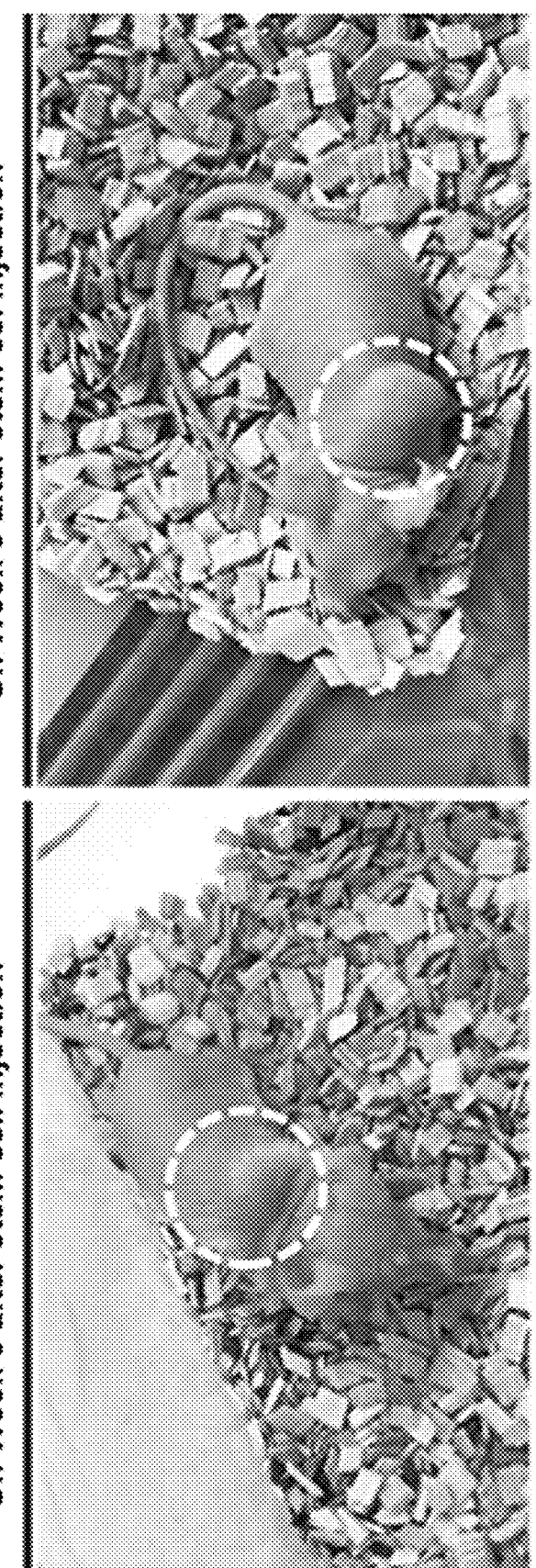
FIG. 5A is a picture confirming that teratoma is formed when porcine embryonic stem cells are infused into nude mice.
Figure 5B:
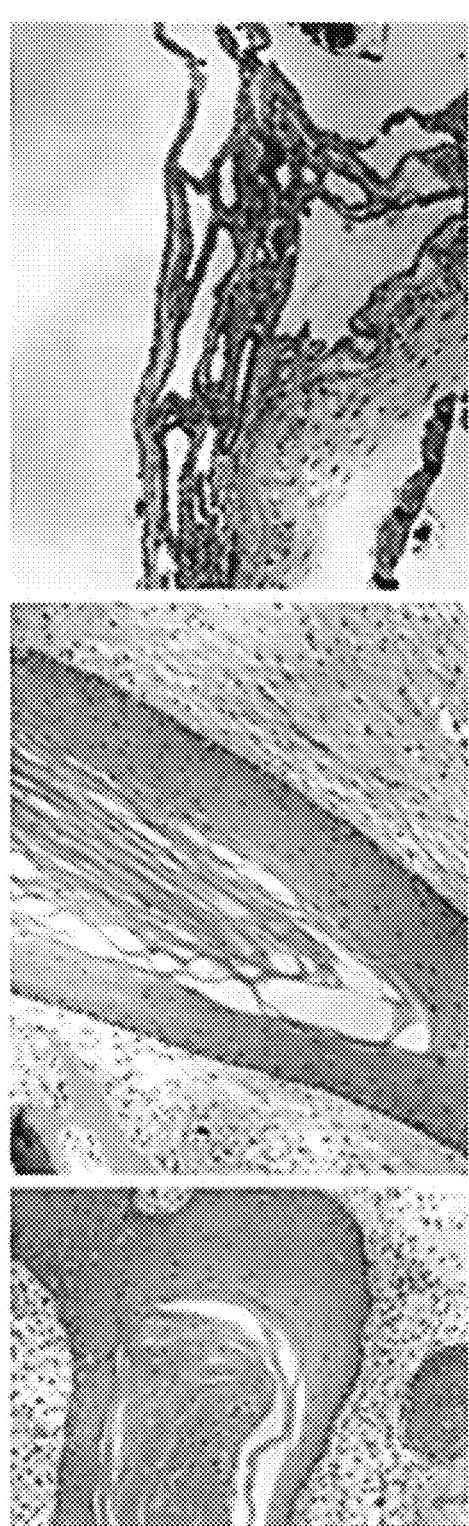
FIG. 5B is a photograph confirming the formation of teratoma by histological analysis.

(Example 7) Confirmation of Teratoma-forming Capacity for Verification of Pluripotency of Porcine Embryonic Stem Cells Porcine embryonic stem cells were treated with 10 μM of Y-27632 for 3 hours and then isolated from feeder cells using a glass pipette and washed with Dulbecco's phosphate-buffered saline (DPBS; Welgene). The washed embryonic stem cell line was treated with Gentle Cell Dissociation Reagent (STEMCELL Technologies) for 4 minutes and cut into small pieces by manipulation with a pipette. Only the cells were isolated through centrifugation (2,000 rpm, 3 minutes), and then they were re-suspended in a 50 μl maintenance culture solution including 20 μM of Y-27632 and mixed with 50 μl of Matrigel. This was carefully subcutaneously injected into a nude mice using a syringe, and then teratoma formation was confirmed three months later (FIGS. 5A and 5B).

(Example 8) Directed Differentiation into Neural Cell and Cardiomyocytes

1. In the case of neural cells, a STEMDIFF™ Neural Induction Medium (STEMCELL Technologies) was used.

2. In the case of cardiomyocytes, the procedure was performed with reference to the paper "Human embryonic stem cells can differentiate into myocytes with structural and functional properties of cardiomyocytes, 2001".

Figure 6A:
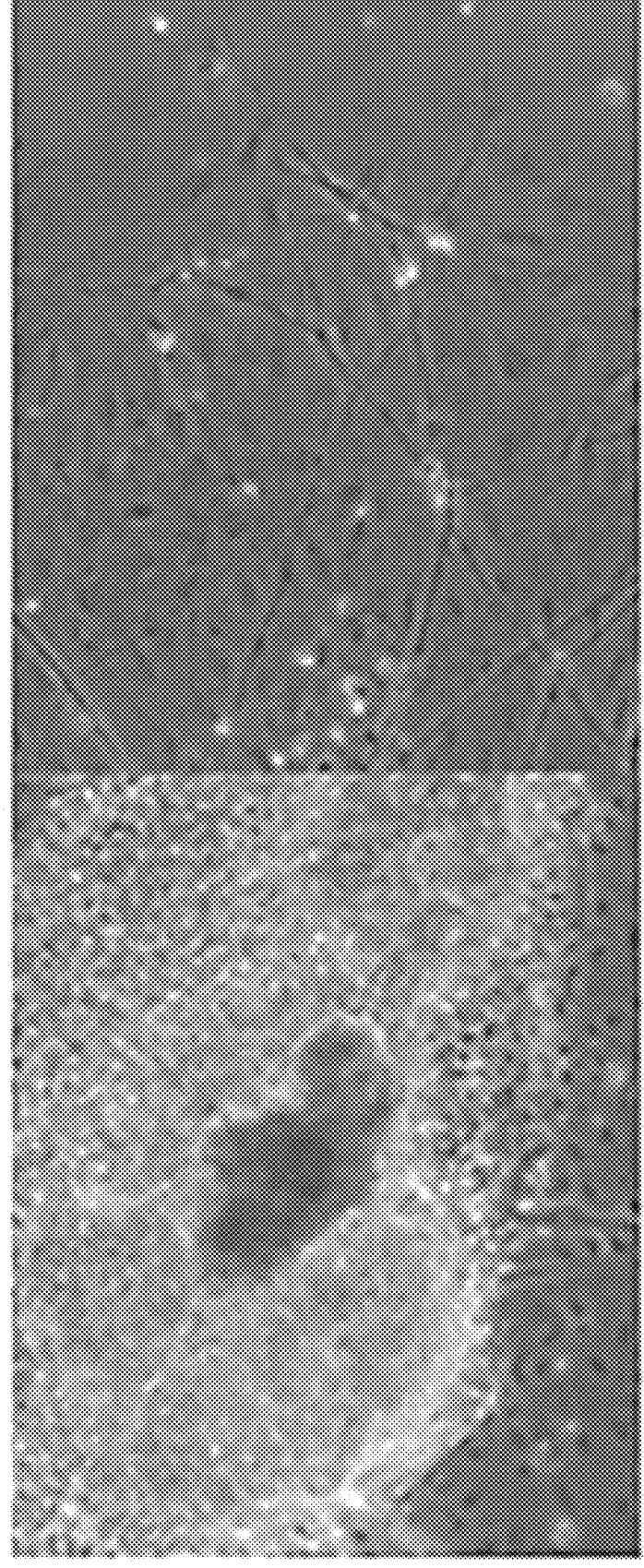
FIGS. 6A and 6B are pictures of directed differentiation of porcine embryonic stem cells into neural cells.
Figure 6B:
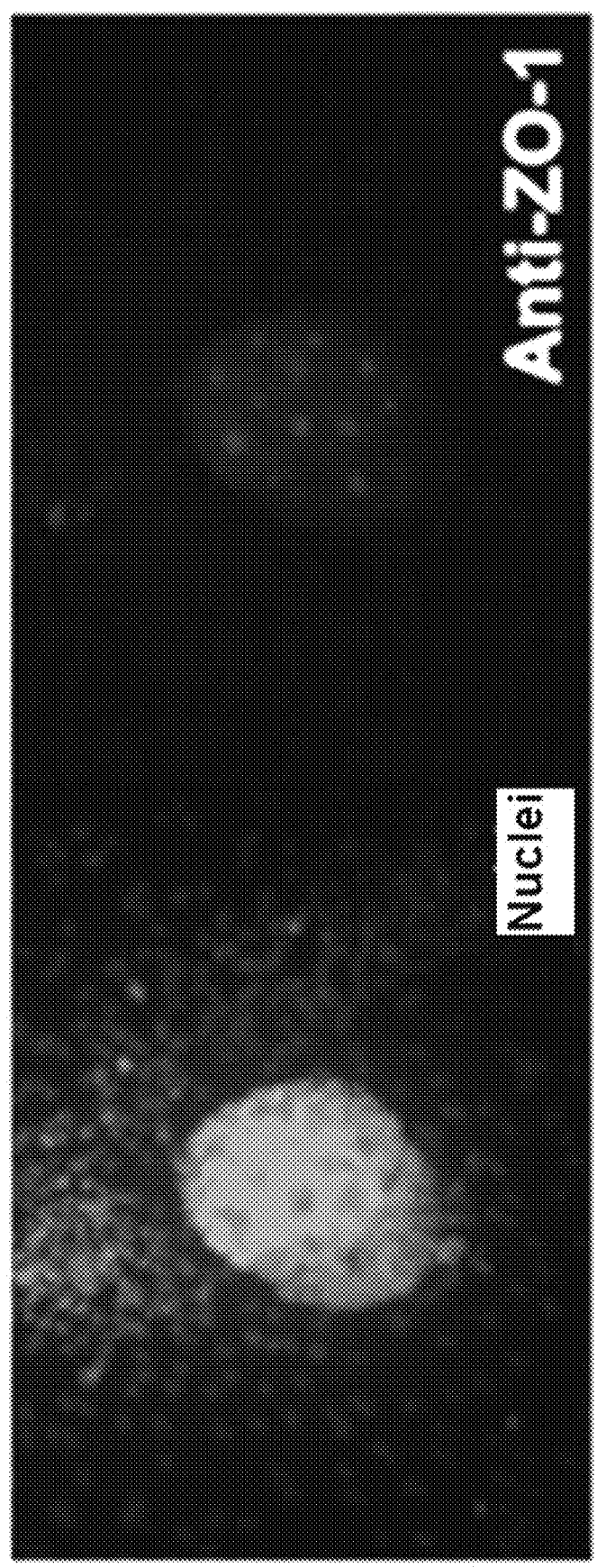

As a result of differentiation according to the previously reported protocol established in human stem cells, porcine embryonic stem cells were differentiated into neural cells and cardiomyocytes. For neural cell differentiation, the petal-shaped structure of the neural rosette was confirmed (FIGS. 6A and 6B), and the structure of the neurons was also confirmed. In the case of cardiomyocytes, the cluster of cells that spontaneously contract and relax during differentiation was found. This showed that porcine embryonic stem cells established in this study have similar characteristics to human stem cells and can be utilized for preclinical studies.

What is claimed is:
1. A culture medium composition for culturing porcine pluripotent stem cells, comprising:
   a. the culture medium composition comprising
   $3.03 \times 10^{-4}$ to $6.06 \times 10^{-3}$ μM basic fibroblast growth factor (bFGF);
   $1.50 \times 10^{-4}$ to $5.40 \times 10^{-4}$ μM Activin A;
   0.5 to 2.50 μM CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile); and

1.20 to 3.00 µM IWR-1 (4-(1,3,3a,4,7,7a-Hexahydro-1, 3-dioxo-4,7-methano-2H-isoindol-2-yl)-N-8-quinoli-nyl-Benzamide), and b. porcine pluripotent stem cells, wherein the culture medium composition is free of fetal bovine serum and the culture medium composition is capable of maintaining porcine pluripotent stem cells in an undifferentiated state and allowing for their long-term cryopreservation, and wherein the culture medium composition has the ability to maintain the pluripotent stem cells in an undifferentiated state with in vivo differentiation capacity, and the porcine pluripotent stem cells cultured in the culture medium composition form teratomas and/or chimeras.

2. The culture medium composition of claim 1, wherein the culture medium further comprises Dulbecco's Modified Eagle's Medium (DMEM) comprising a serum replacement, lipid concentrate (LC), L-arginine and/or L-glutamine, Modified Eagle's Medium (MEM) nonessential amino acids, antibacterial agents, antifungal agents, and beta-mercaptoethanol.

3. The culture medium composition of claim 1, comprising:

about $6.06 \times 10^{-4}$ µM bFGF;

about $3.85 \times 10^{-4}$ µM Activin A;

about 0.5 µM CHIR99021; and about 1.5 µM IWR-1, and wherein the culture medium further comprises Dulbecco's Modified Eagle's Medium (DMEM) comprising about 20% (v/v) of bovine serum replacement; about 0.1% (v/v) of lipid concentrate (LC); about 1% (v/v) of L-arginine and/or L-glutamine; about 1% (v/v) of Modified Eagle's Medium (MEM) nonessential amino acids; about 1% (v/v) of antibiotics-antimycotics; and about 0.1 mM β-mercaptoethanol.

4. The culture medium composition of claim 1, wherein the culture medium is Dulbecco's Modified Eagle's Medium (DMEM) comprising about 15% (v/v) of the serum replacement; about 0.1% (v/v) of the lipid concentrate (LC); about 1% (v/v) of L-arginine and/or L-glutamine; about 1% (v/v) of Modified Eagle's Medium (MEM) nonessential amino acids; about 1% (v/v) of antibiotics-antimycotics; about 0.1 mM β-mercaptoethanol; about $1.21 \times 10^{-3}$ µM bFGF; about $3.85 \times 10^{-4}$ µM activin A; about 1.5 µM CHIR99021; and about 2.5 µM IWR-1.

5. A cryopreservation composition for cryopreserving porcine pluripotent stem cells, the cryopreservation composition comprising about 10% (v/v) of dimethyl sulfoxide (DMSO), about 10% (v/v) of ethylene glycol, and about 80% (v/v) of the culture medium composition according to claim 4.

6. A cryopreservation composition for cryopreserving porcine pluripotent stem cells, the cryopreservation composition comprising about 20% (v/v) of dimethyl sulfoxide (DMSO), about 20% (v/v) of ethylene glycol, about 0.5M sugar, and about 60% (v/v) of the culture medium composition according to claim 4.

7. A method for culturing porcine pluripotent stem cells comprising culturing the porcine pluripotent stem cells in the culture medium composition according to claim 1.

8. A method for maintaining porcine pluripotent stem cells comprising maintaining the porcine pluripotent stem cells in the culture medium composition of claim 1.

9. A method for preserving porcine pluripotent stem cells comprising preserving the porcine pluripotent stem cells in the culture medium composition of claim 1.

10. The culture medium composition of claim 2, wherein the culture medium is DMEM comprising about 20% (v/v) of the serum replacement; about 0.1% (v/v) of the LC; about 1% (v/v) of L-arginine-L-glutamine; about 1% (v/v) of MEM nonessential amino acids; about 1% (v/v) of antibiotics-antimycotics; about 0.1 mM β-mercaptoethanol; about $6.06 \times 10^{-4}$ µM bFGF; about $3.85 \times 10^{-4}$ µM Activin A; about 0.5 µM CHIR99021; and about 1.5 µM IWR-1.

11. The culture medium composition of claim 1, wherein the culture medium is DMEM comprising about 15% (v/v) of the serum replacement; about 0.1% (v/v) of the LC; about 1% (v/v) of L-arginine-L-glutamine; about 1% (v/v) of MEM nonessential amino acids; about 1% (v/v) of antibiotics-antimycotics; about 0.1 mM β-mercaptoethanol; about $1.21 \times 10^{-3}$ µM bFGF; about $3.85 \times 10^{-4}$ µM activin A; about 1.5 µM CHIR99021; and about 2.5 µM IWR-1.

12. A cryopreservation composition for cryopreserving porcine pluripotent stem cells, the cryopreservation composition comprising about 10% (v/v) of dimethyl sulfoxide (DMSO), about 10% (v/v) of ethylene glycol, and about 80% (v/v) of the culture medium composition according to claim 11.

13. A cryopreservation composition for cryopreserving porcine pluripotent stem cells, the cryopreservation composition comprising about 20% (v/v) of dimethyl sulfoxide (DMSO), about 20% (v/v) of ethylene glycol, about 0.5M sugar, and about 60% (v/v) of the culture medium composition according to claim 11.

14. A method for culturing porcine pluripotent stem cells comprising culturing the porcine pluripotent stem cells in the culture medium composition according to claim 2.

15. A method for maintaining porcine pluripotent stem cells comprising maintaining the porcine pluripotent stem cells in the culture medium composition of claim 2.

16. A method for preserving porcine pluripotent stem cells comprising preserving the porcine pluripotent stem cells in the culture medium composition of claim 2.

17. The culture medium composition according to claim 1, wherein the culture medium composition has an ability to maintain pluripotency of the porcine pluripotent stem cells, and the porcine pluripotent stem cells cultured in the culture medium composition express SSEA4, TRA-1-60 and TRA-1-81.

* * * * *